(12) United States Patent
Saunders

(10) Patent No.: US 7,824,437 B1
(45) Date of Patent: Nov. 2, 2010

(54) MULTI-FUNCTIONAL ABDOMINAL CRAMP REDUCING DEVICE AND ASSOCIATED METHOD

(76) Inventor: Gina Saunders, 15805 Millbrook La., Laurel, MD (US) 20707

( * ) Notice: Subject to any disclaimer, the term of this patent is extended or adjusted under 35 U.S.C. 154(b) by 893 days.

(21) Appl. No.: 11/706,741

(22) Filed: Feb. 13, 2007

Related U.S. Application Data

(60) Provisional application No. 60/772,966, filed on Feb. 13, 2006.

(51) Int. Cl.
*A61F 7/00* (2006.01)

(52) U.S. Cl. .................. 607/108; 607/112; 219/211; 601/15

(58) Field of Classification Search .......... 607/108, 607/112; 219/211
See application file for complete search history.

(56) References Cited

U.S. PATENT DOCUMENTS 3,680,563 A * 8/1972 Forrest .................. 607/112
4,628,930 A 12/1986 Williams
5,913,834 A * 6/1999 Francais .................. 600/591
6,235,049 B1 5/2001 Nazerian
6,308,341 B1 10/2001 Shelton
6,554,787 B1 4/2003 Griffin
2004/0143199 A1* 7/2004 Cotterell-Grant et al. ..... 601/15

* cited by examiner

*Primary Examiner*—Roy D Gibson
*Assistant Examiner*—Kaitlyn E Helling

(57) ABSTRACT

A portable electronic device for reducing periodic cramping about an abdominal cavity of a user during a menstrual cycle includes an elastic panty garment, a controller removably attached directly to an outer surface of the panty garment and a plurality of electro-mechanical transducers generating output vibrations, and a plurality of heatable magnetic straps directly coupled to the outer surface of the panty garment. The heatable magnetic straps extend along anterior and posterior faces of the panty garment and are simultaneously actuated to a desired temperature level while the transducers are actuated to an on position. The heatable magnetic straps being freely movable along the outer surface of the panty garment while the transducers are nested within respective pouches.

12 Claims, 9 Drawing Sheets

MULTI-FUNCTIONAL ABDOMINAL CRAMP REDUCING DEVICE AND ASSOCIATED METHOD

CROSS REFERENCE TO RELATED APPLICATIONS

This application claims the benefit of U.S. Provisional Application No. 60/772,966, filed Feb. 13, 2006, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to massaging and heating devices and, more particularly, to a portable garment embedded with heating and massaging mechanisms that are selectively controlled by a user to alleviate abdominal cramping occurring during a women's menstrual cycle.

2. Prior Art

A regular menstrual cycle is a normal fact of life for most healthy adolescent girls and adult women. The monthly shedding f the lining of the uterus, the menstrual cycle or "period" as it is also known, is an important aspect of a woman's fertility. Providing a cushiony, nutrient-rich bed for a fertilized egg to grow into a baby, the uterine lining slowly develops during the course of a month in anticipation of the egg's arrival. Although an egg is released every month from one of a woman's two ovaries, the majority of time this egg remains unfertilized. Simply dissolving the after being dropped from the ovary, the egg and the lining are released from the body typically over the course of three to five days. A woman's menstrual cycle can begin as early as the age of nine and can last well into her fifties. For many women, a normal menstrual cycle is accompanied by uncomfortable side effects.

Specifically, many women experience pain and discomfort during their menstrual cycle. While some women experience only moderate pain and light cramping during their monthly period, others suffer much more serious complications. In particular, extreme lower back pain and excruciating abdominal cramps go hand in hand with a monthly period for many women. This pain can be so debilitating that many women who suffer severe menstrual symptoms literally "shut down" during their period, force to miss days of work, school or even planned social engagements, simply because the pain is too great to get out of bed.

Prior art attempts have been made to alleviate the pain associated with menstrual cycle cramping. One prior art example is disclosed in U.S. Pat. No. 4,628,930 to Williams, which discloses a girdle for use in preventing the discomfort of cramps due to a menstrual period. The girdle has a cotton cloth panty of a type having a front portion, a rear portion and interconnecting side portions. The panty has a continuous elastic material around the top thereof and has a battery holding compartment attached to the top to a central front portion thereof. An electrical resistance heating structure is attached to the outside of the cotton panty front portion and extends from the crotch portion thereof an upwardly and outwardly in a V-shaped configuration to where the battery holding compartment is attached to the elastic. An electric battery is removably disposed of the battery holding compartment. A V-shaped basket weave cloth structure having a higher R-value than that of the cotton cloth of which the front portion is constructed is disposed over the front of the electrical heating structure for causing heat from the electrical heating structure to tend to flow through the cotton front panel towards the person wearing the girdle rather than through the front basket weave cloth whereby such person wearing the girdle will have that part of her anatomy which tends to cramp during menstrual periods heated during a menstrual period. Unfortunately, such a prior art example does not provide therapeutic vibrating and magnetic waves.

Another prior art example is disclosed in U.S. Pat. No. 6,019,782 to Davis et al., which teaches a disposable thermal body pad comprising one or more thermal packs having a unified structure of at least one continuous layer of a semi rigid material which softens when heated and a plurality of individual heat cells, spaced apart and fixed within or to the unified structure of the thermal pack. The disposable thermal body pads are intended to be attached to a user's clothing on one side and to be held directly against the user's skin on the other side. More particularly, the present invention relates to disposable thermal body pads having good conformity to user's body which provides consistent, convenient and comfortable heat application. Even more particularly, the present invention relates to such disposable thermal body pads intended for relieving menstrual pain. Such a manner of alleviating pain does not provide vibrating motions coupled with exposure to a magnetic field about the abdominal cavity.

Accordingly, a need remains for a portable garment embedded with heating and massaging mechanisms that are selectively controlled by a user to alleviate abdominal cramping during a woman's menstrual cycle while also providing magnetic therapy to the bone structure and surrounding muscles.

BRIEF SUMMARY OF THE INVENTION

In view of the foregoing background, it is therefore an object of the present invention to provide a portable garment embedded with heating and massaging mechanisms that are selectively controlled by a user to alleviate abdominal cramping during a woman's menstrual cycle while also providing magnetic therapy to the bone structure and surrounding muscles. These and other objects, features, and advantages of the invention are provided by a portable electronic device for reducing periodic cramping about an abdominal cavity of a user during menstrual cycles.

In a preferred embodiment, the electronic device includes a panty garment formed from elastic material and having a plurality of pouches mated directly to an inner surface such that the pouches are invisible from an exterior of the panty garment thereof. The panty garment is formed from water impermeable and washable material for repeated use in an aqueous environment. A controller is removably attached directly to an outer surface of the panty garment. The controller includes a power source and a user interface electrically coupled thereto. The heatable magnetic straps preferably include an outer membrane formed from elastic material such that each strap can be snuggly configured against a contour of the user's body while preventing undesirable movement therealong.

A plurality of electro-mechanical transducers that generate output vibrations are removably seated within the pouches and juxtaposed along a major surface area of the panty garment such that output vibrations are distributed through out anterior and posterior faces of the abdominal cavity. A plurality of heatable magnetic straps are directly coupled to the outer surface of the panty garment and extend along an entire perimeter thereof such that the heatable magnetic straps continuously extend about the anterior and posterior faces of the panty garment.

The heatable magnetic straps are simultaneously actuated to a desired temperature level while the transducers are actuated to an on position. Such heatable magnetic straps being freely movable along the outer surface of the panty garment while the transducers are nested within the pouches. In a preferred embodiment, each of the heatable magnetic straps includes first and second isolated chambers formed along an entire longitudinal length thereof.

A flexible magnetic core member is removably seated within the first chamber and extending along an entire longitudinal length thereof and a deformable resistance wire is adjustably positioned within the second chamber. The resistance wire is critically and advantageously adaptable to alternate configurations while nested within the second chamber such that heat is discharged at alternate partial segments within the second chamber without interrupting a continuous magnetic force emanating along an entire longitudinal length of the first chamber. Accordingly, the resistance wire can be curled into various sizes and shapes while seated within its respective chamber by simply maneuvering the resistance wire with the user's fingers and bunching the wire towards one end of the chamber as need during operating conditions. Such a feature overcomes prior art shortcomings of inadequately supplying heat to target zones along the abdominal cavity.

The present invention further discloses a method for treating cramping muscles occurring along an abdominal cavity of a user. The method includes the steps of providing a panty garment formed from elastic material and having a plurality of pouches mated directly to an inner surface such that the pouches are invisible from an exterior of the panty garment; positioning the panty garment about the abdominal cavity of the user by inserting both user legs through bottom openings formed within the panty garment; removably attaching a controller directly to an outer surface of the panty garment; removably seating a plurality of electro-mechanical transducers generating output vibrations within the pouches by juxtaposing the transducers along a major surface area of the panty garment such that output vibrations are distributed through out anterior and posterior faces of the abdominal cavity; directly coupling a plurality of heatable magnetic straps to the outer surface of the panty garment by extending the heatable magnetic straps along an entire perimeter thereof such that the heatable magnetic straps continuously extend about the anterior and posterior faces of the panty garment; actuating the heatable magnetic straps to a desired temperature level while simultaneously actuating the transducers to an on position; and, freely moving the heatable magnetic straps along the outer surface of the panty garment while the transducers are nested within the pouches. The combination of steps advantageously allow a user to adjustably position the heatable magnetic straps along the abdominal cavity while the transducers continuously vibrate so that the user simultaneously receives heat, vibration and magnetic therapy as needed.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

Figure 1:
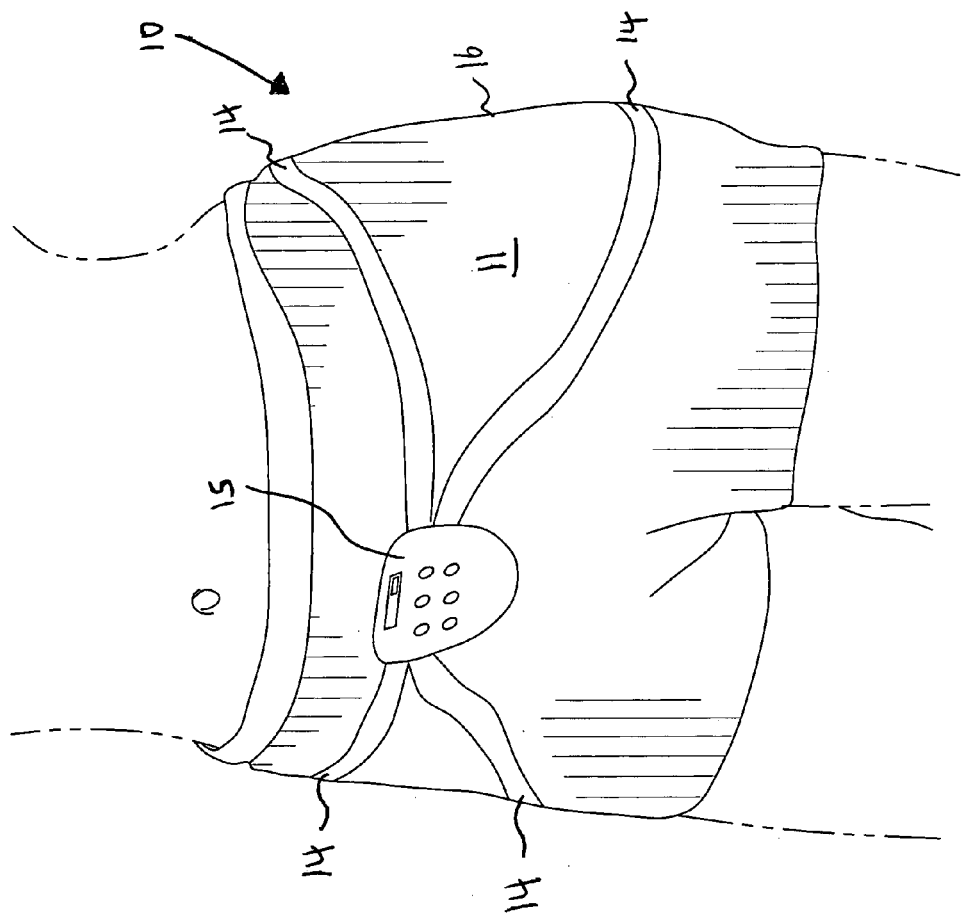
FIG. 1 is a front perspective view showing a portable garment embedded with heating and massaging mechanisms that are selectively controlled by a user to alleviate abdominal cramping during a woman's menstrual cycle while also providing magnetic therapy to the bone structure and surrounding muscles, in accordance with the present invention.
Figure 2:
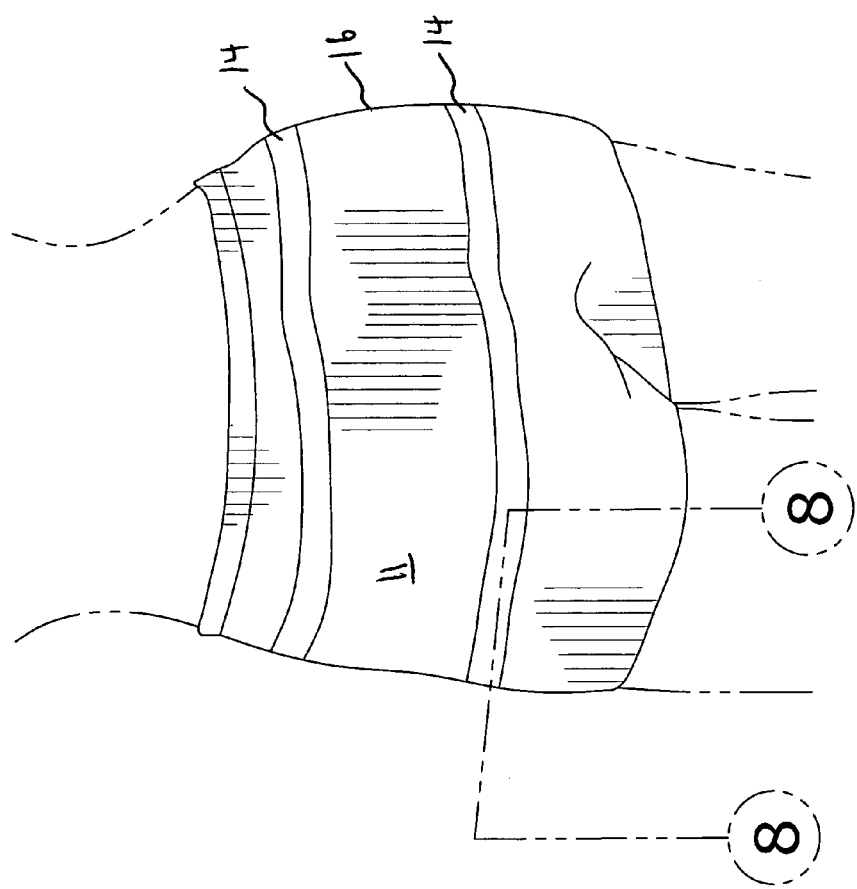
FIG. 2 is a rear perspective view of FIG. 1 showing the heatable magnetic straps wrapped about a posterior face of a user's buttock.
Figure 3:
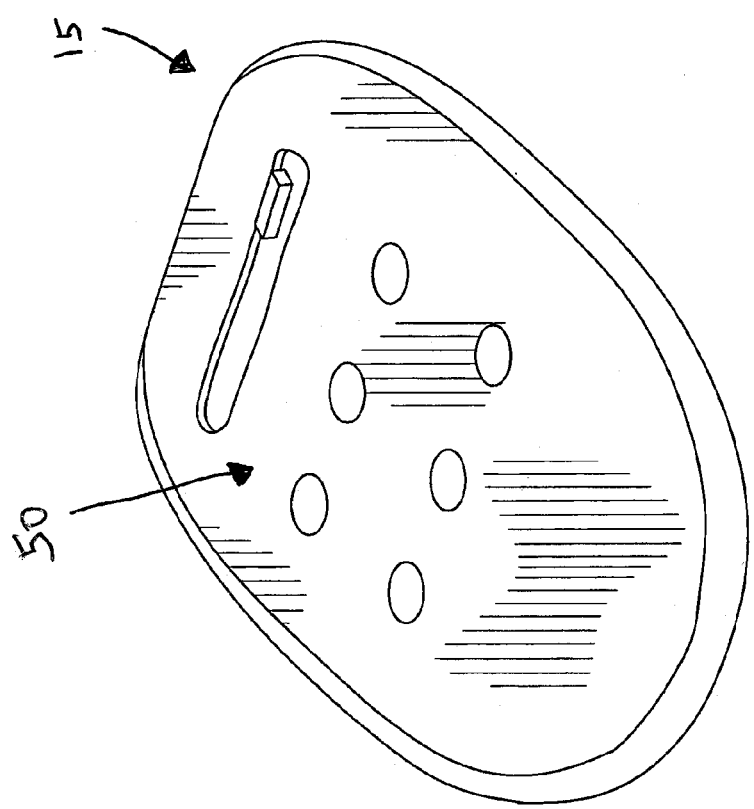
FIG. 3 is a perspective view of the wireless controller employed by the present invention.
Figure 4:
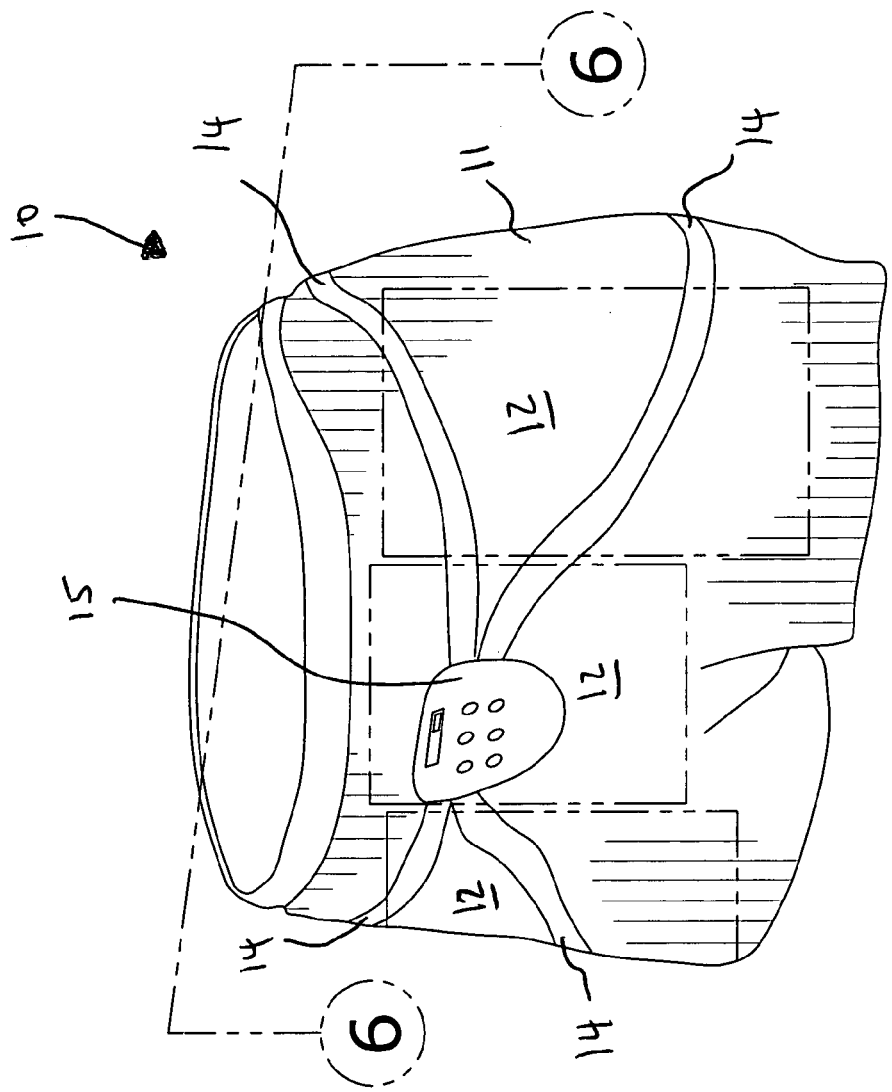
FIG. 4 is a front perspective view showing the hidden shapes of the pouches formed along the interior of the panty garment.
Figure 5:
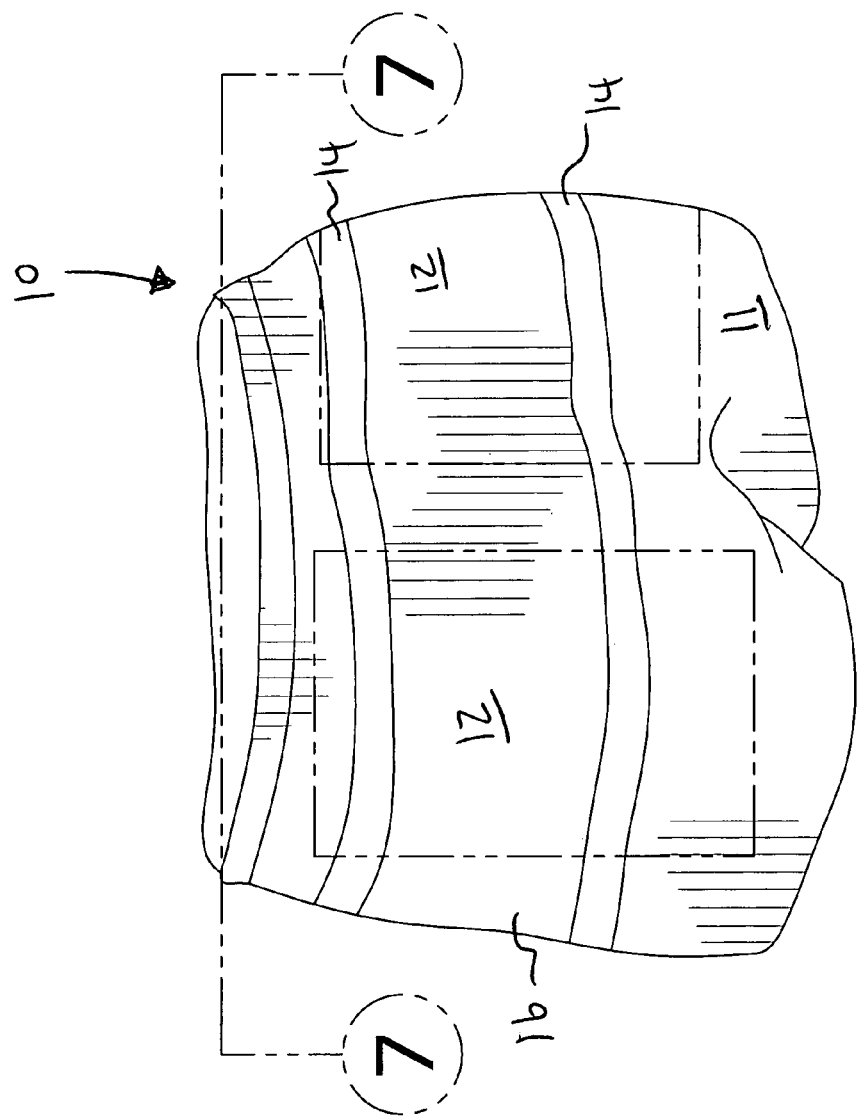
FIG. 5 is a rear perspective view of FIG. 4.

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The device of this invention is referred to generally in FIGS. 1-9b by the reference numeral 10 and is intended to provide a portable garment embedded with heating and massaging mechanisms that are selectively controlled by a user to alleviate abdominal cramping during a woman's menstrual cycle while also providing magnetic therapy to the bone structure and surrounding muscles. It should be understood that the device 10 may be used to provide therapeutic healing for many areas of the user's body and, therefore, should not be construed as limited to use only on the abdominal cavity.

In a preferred embodiment, the electronic device 10 includes a panty garment 11 formed from elastic material and having a plurality of pouches 12 mated directly to an inner surface 13 such that the pouches 12 are invisible from an exterior of the panty garment 11, as best shown in FIGS. 4-7. The pouches 12 are critically formed along the interior surface 13 of the panty garment 11 and are accessible only from the inside of the panty garment 11. The panty garment 11 is formed from water impermeable and washable material for repeated use in an aqueous environment. Suitable materials may include deformably resilient elastomeric materials which have altering rigidity when heat is applied thereto. Thus, when heatable magnetic straps 14 (described hereinbelow) are toggled to an elevated temperature, the panty garment 11 becomes more stretchable and less resilient during use for providing comfort to the user.

Referring to FIGS. 1, 3, 4, 9a and 9b, a controller 15 is removably attached directly to an outer surface 16 of the panty garment 11. Various multi-functional infrared red signal generating controllers may be employed, as well known in the industry, which can modulate and demodulate the signals into desired frequencies. A conventional power source (not source), such as a battery pack, and a user interface 16 electrically coupled to the controller 15 such that the user can manually toggle heat and vibration functions as needed during operation.

Figure 6:
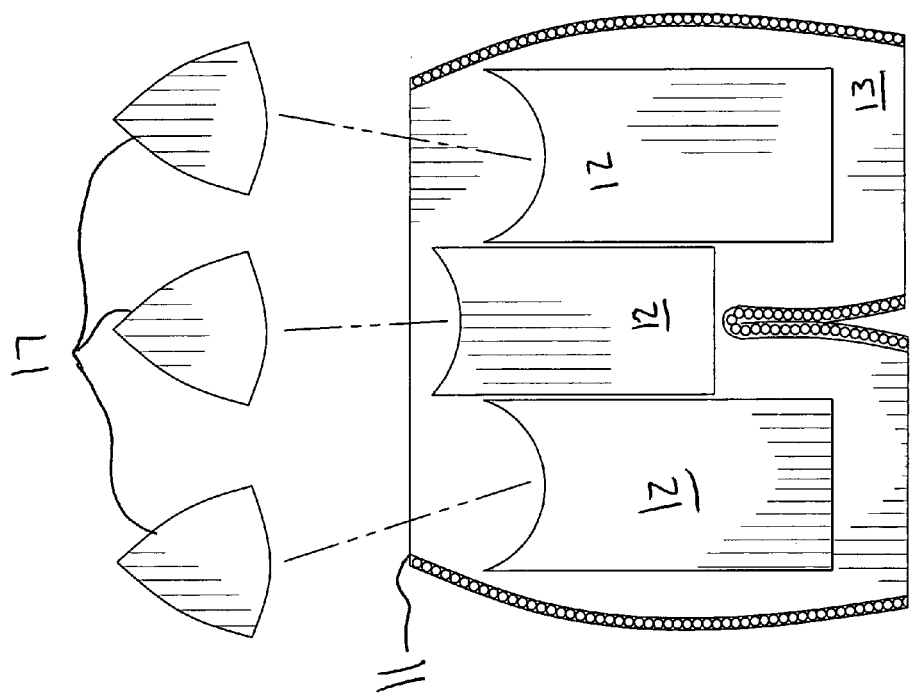
FIG. 6 is a cross-sectional view of the panty garment showing selected ones of the transducers removably positioned within their respective pouches on an anterior face of the panty garment.
Figure 7:
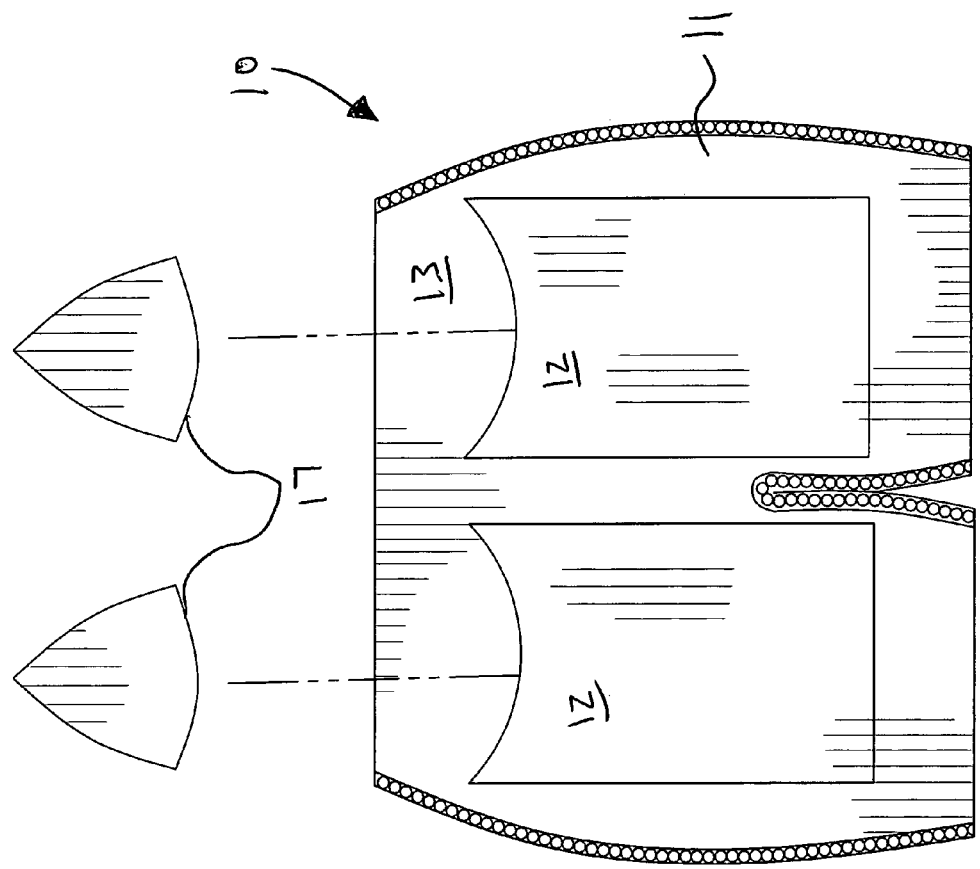
FIG. 7 is a cross-sectional view of the panty garment showing selected ones of the transducers removably positioned within their respective pouches on a posterior face of the panty garment.

Referring to FIGS. 6 and 7, a plurality of electro-mechanical transducers 17 that generate output vibrations are removably seated within the pouches 12 and juxtaposed along a major surface area of the panty garment 11 such that output vibrations are distributed through out anterior and posterior faces of the abdominal cavity. The transducers 17 are interfaced with respective receivers and tuned frequency filtering circuits for deciphering the various infrared signals generated by the controller 15 and thereby filtering unwanted frequency signals from nearby signal generating sources. One skilled in the art understands that various piezoelectric transducers or electro-mechanical actuators may be employed by the present invention so long as such devices do not interfere with the magnetic field of the magnet 21 (described hereinbelow) seated within the pouches 12 of the heatable magnetic straps 14 (described hereinbelow).

As perhaps best shown in FIGS. 1, 2, 9a and 9b, the plurality of heatable magnetic straps 14 are directly coupled to the outer surface 16 of the panty garment 11 and extend along an entire perimeter thereof such that the heatable magnetic straps 14 continuously extend about the anterior and posterior faces of the panty garment 11. The heatable magnetic straps 14 preferably include an outer membrane 18 formed from elastic material such that each strap can be snuggly configured against a contour of the user's body while preventing undesirable movement therealong. The outer membrane 18 is preferably formed from heat-conductive material for evenly distributing heat through the entire length of the straps respectively. The controller 15 may be programmed so that the heatable magnetic straps 14 become simultaneously actuated to a desired temperature level while the transducers 17 are actuated to an on position. Such heatable magnetic straps 14 are freely movable along the outer surface 16 of the panty garment 11 while the transducers 17 are nested within the pouches 12 to thereby allow the user to manually adjust a position of the straps 14 along the most discomforting areas.

Figure 8:
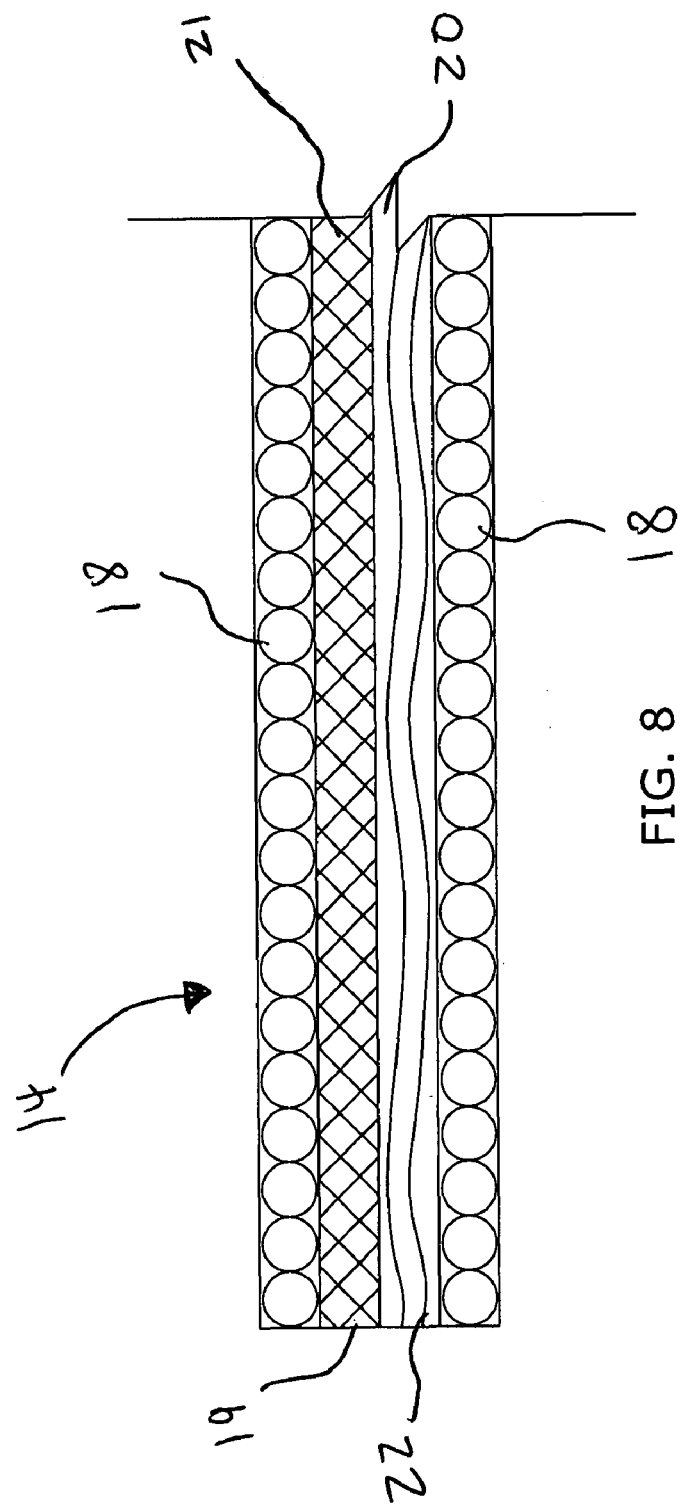
FIG. 8 is a cross-sectional view taken along one of the heatable magnetic straps showing the magnet and the flexible resistance wire seated therein.
Figures 9A, 9B:
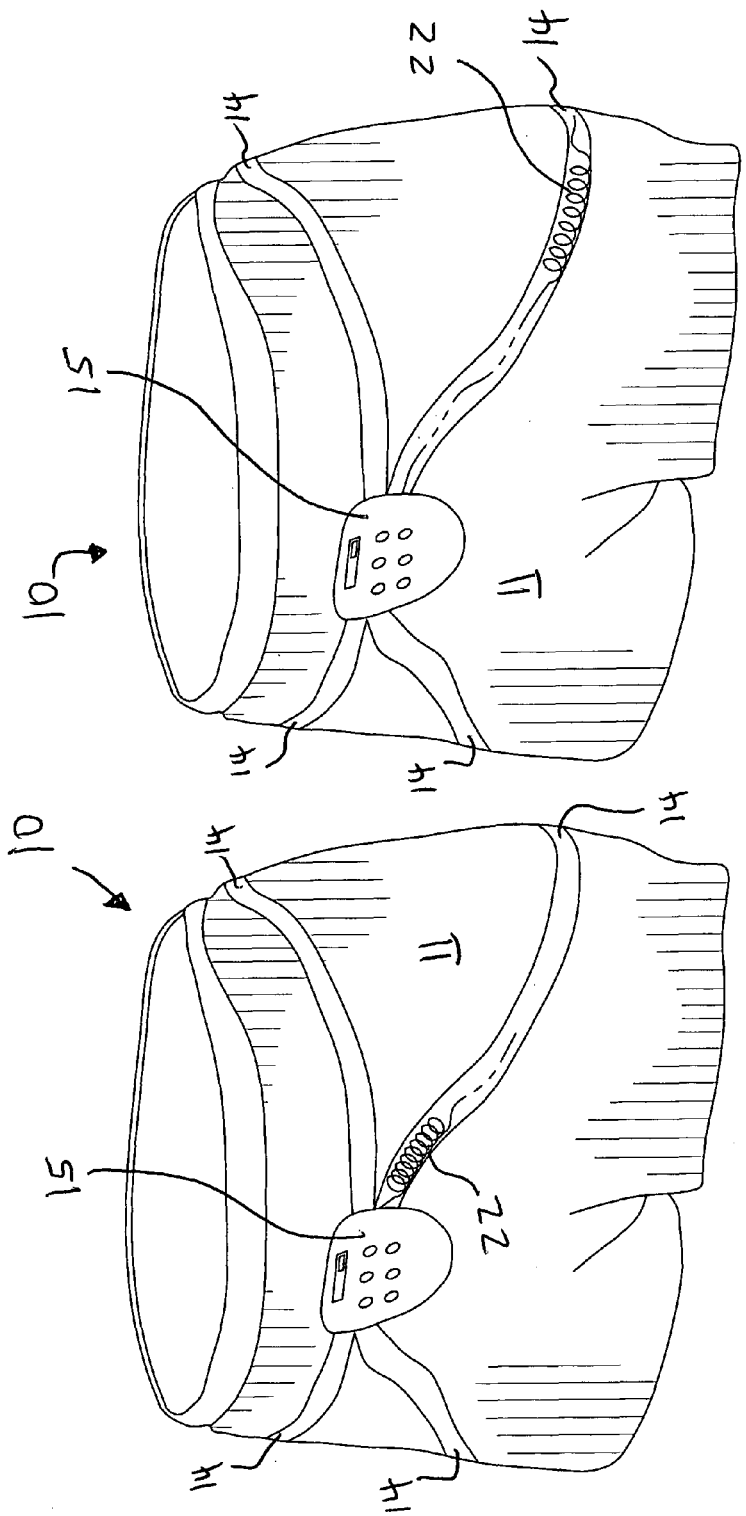
FIGS. 9a and 9b are front perspective views showing the resistance wire adapted to alternate positions within the heatable magnetic straps.

As best shown in FIGS. 8, 9a, and 9b, each of the heatable magnetic straps 14 includes first and second isolated chambers 19, 20 formed along an entire longitudinal length thereof. A flexible magnetic core member 21 is removably seated within the first chamber 19 and extends along an entire longitudinal length thereof. A deformable resistance wire 22 is adjustably positioned within the second chamber 20. The resistance wire 22 is critically and advantageously adaptable to alternate configurations while nested within the second chamber 20 such that heat is discharged at alternate partial segments within the second chamber 20 without interrupting a continuous magnetic force emanating along an entire longitudinal length of the first chamber 19. Accordingly, the resistance wire 22 can be curled into various sizes and shapes while seated within its respective chamber by simply maneuvering the resistance wire 22 with the user's fingers and bunching the wire towards one end of the chamber 20 as need during operating conditions. Such a feature overcomes prior art shortcomings of inadequately supplying heat to target zones along the abdominal cavity.

When an electric current moves through the resistance wire 22, a resulting magnetic field is directed according to the "right hand rule." If the right hand is used as a model, and the thumb of the right hand points along the wire from positive towards the negative side ("conventional current", the reverse of the direction of actual movement of electrons), then the magnetic field will wrap around the wire in the direction indicated by the fingers of the right hand. If a loop or helix of wire is formed such that the current is traveling in a circle, then all of the field lines in the center of the loop are directed in the same direction, resulting in a magnetic dipole whose strength depends on the current around the loop, or the current in the helix multiplied by the number of turns of wire. In the case of such a loop, if the fingers of the right hand are directed in the direction of conventional current flow (i.e., positive to negative, the opposite direction to the actual flow of electrons), the thumb will point in the direction corresponding to the North pole of the dipole. Thus, the combined electromagnetic force of the resistance wire 22 and the magnetic core member 21 seated within the straps 14, cooperate together and provide an unexpected benefit of relieving muscle aches and cramps along the cervical region of the user.

The present invention further discloses a method for treating cramping muscles occurring along an abdominal cavity of a user. The method includes the steps of providing a panty garment 11 formed from elastic material and having a plurality of pouches 12 mated directly to an inner surface 13 such that the pouches 12 are invisible from an exterior of the panty garment 11; positioning the panty garment 11 about the abdominal cavity of the user by inserting both user legs through bottom openings formed within the panty garment 11; removably attaching a controller 15 directly to an outer surface of the panty garment 11; removably seating a plurality of electro-mechanical transducers 17 generating output vibrations within the pouches 12 by juxtaposing the transducers 17 along a major surface area of the panty garment 11 such that output vibrations are distributed through out anterior and posterior faces of the abdominal cavity; directly coupling a plurality of heatable magnetic straps 14 to the outer surface of the panty garment 11 by extending the heatable magnetic straps 14 along an entire perimeter thereof such that the heatable magnetic straps 14 continuously extend about the anterior and posterior faces of the panty garment 11; actuating the heatable magnetic straps 14 to a desired temperature level while simultaneously actuating the transducers 17 to an on position; and, freely moving the heatable magnetic straps 14 along the outer surface of the panty garment 11 while the transducers 17 are nested within the pouches 12. Such a sequence and combination of steps advantageously allow a user to adjustably position the heatable magnetic straps 14 along the abdominal cavity while the transducers 17 continuously vibrate so that the user simultaneously receives heat, vibration and magnetic therapy as needed.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A portable electronic device for reducing periodic cramping about an abdominal cavity of a user during a menstrual cycle, said electronic device comprising:
    a panty garment formed from elastic material and having a plurality of pouches mated directly to an inner surface such that said pouches are invisible from an exterior of said panty garment thereof;
    a controller removably attached directly to an outer surface of said panty garment;
    a plurality of electro-mechanical transducers generating output vibrations, said transducers being removably seated within said pouches and juxtaposed along a major surface area of said panty garment such that output vibrations are distributed through out anterior and posterior faces of the abdominal cavity; and
    a plurality of heatable magnetic straps being directly coupled to said outer surface of said panty garment and extending along an entire perimeter thereof such that said heatable magnetic straps continuously extend about said anterior and posterior faces of said panty garment;
    wherein said heatable magnetic straps are simultaneously actuated to a desired temperature level while said transducers are actuated to an on position, said heatable magnetic straps being freely movable along said outer surface of said panty garment while said transducers are nested within said pouches.

2. The electronic device of claim 1, wherein said heatable magnetic straps comprise: an outer membrane formed from elastic material.

3. The electronic device of claim 1, wherein each of said heatable magnetic straps comprises:
    first and second isolated chambers formed along an entire longitudinal length thereof;
    a flexible magnetic core member removably seated within said first chamber and extending along an entire longitudinal length thereof; and
    a deformable resistance wire adjustably positioned within said second chamber;
    wherein said resistance wire is adaptable to alternate configurations while nested within said second chamber such that heat is discharged at alternate partial segments within said second chamber without interrupting a continuous magnetic force emanating along an entire longitudinal length of said first chamber.

4. The electronic device of claim 1, wherein said panty garment is formed from water impermeable and washable material for repeated use in an aqueous environment.

5. A portable electronic device for reducing periodic cramping about an abdominal cavity of a user during a menstrual cycle, said electronic device comprising:
    a panty garment formed from elastic material and having a plurality of pouches mated directly to an inner surface such that said pouches are invisible from an exterior of said panty garment thereof;
    a controller removably attached directly to an outer surface of said panty garment;
    a plurality of electro-mechanical transducers generating output vibrations, said transducers being removably seated within said pouches and juxtaposed along a major surface area of said panty garment such that output vibrations are distributed through out anterior and posterior faces of the abdominal cavity; and
    a plurality of heatable magnetic straps being directly coupled to said outer surface of said panty garment and extending along an entire perimeter thereof such that said heatable magnetic straps continuously extend about said anterior and posterior faces of said panty garment;
    wherein said heatable magnetic straps are simultaneously actuated to a desired temperature level while said transducers are actuated to an on position, said heatable magnetic straps being freely movable along said outer surface of said panty garment while said transducers are nested within said pouches;
    wherein said controller comprises: a power source and a user interface electrically coupled thereto.

6. The electronic device of claim 5, wherein said heatable magnetic straps comprise: an outer membrane formed from elastic material.

7. The electronic device of claim 5, wherein each of said heatable magnetic straps comprises:
    first and second isolated chambers formed along an entire longitudinal length thereof;
    a flexible magnetic core member removably seated within said first chamber and extending along an entire longitudinal length thereof; and
    a deformable resistance wire adjustably positioned within said second chamber;
    wherein said resistance wire is adaptable to alternate configurations while nested within said second chamber such that heat is discharged at alternate partial segments within said second chamber without interrupting a continuous magnetic force emanating along an entire longitudinal length of said first chamber.

8. The electronic device of claim 5, wherein said panty garment is formed from water impermeable and washable material for repeated use in an aqueous environment.

9. A method for treating cramping muscles occurring along an abdominal cavity of a user during a menstrual cycle, said method comprising the steps of:
    a. providing a panty garment formed from elastic material and having a plurality of pouches mated directly to an inner surface such that said pouches are invisible from an exterior of said panty garment thereof;
    b. positioning said panty garment about the abdominal cavity of the user by inserting both user legs through bottom openings formed within said panty garment;
    c. removably attaching a controller directly to an outer surface of said panty garment;

d. removably seating a plurality of electro-mechanical transducers generating output vibrations within said pouches by juxtaposing said transducers along a major surface area of said panty garment such that output vibrations are distributed through out anterior and posterior faces of the abdominal cavity;

e. directly coupling a plurality of heatable magnetic straps to said outer surface of said panty garment by extending said heatable magnetic straps along an entire perimeter thereof such that said heatable magnetic straps continuously extend about said anterior and posterior faces of said panty garment;

f. actuating said heatable magnetic straps to a desired temperature level while simultaneously actuating said transducers to an on position; and g. freely moving said heatable magnetic straps along said outer surface of said panty garment while said transducers are nested within said pouches.

10. The method of claim 9, wherein said heatable magnetic straps comprise: an outer membrane formed from elastic material.

11. The method of claim 9, wherein each of said heatable magnetic straps comprises:

first and second isolated chambers formed along an entire longitudinal length thereof;

a flexible magnetic core member removably seated within said first chamber and extending along an entire longitudinal length thereof; and a deformably resistance wire adjustably positioned within said second chamber;

wherein said resistance wire is adaptable to alternate configurations while nested within said second chamber such that heat is discharged at alternate partial segments within said second chamber without interrupting a continuous magnetic force emanating along an entire longitudinal length of said first chamber.

12. The method of claim 9, wherein said panty garment is formed from water impermeable and washable material for repeated use in an aqueous environment.

\* \* \* \* \*